United States Patent
Kouta et al.

(10) Patent No.: US 8,449,516 B2
(45) Date of Patent: May 28, 2013

(54) STRETCHABLE ABSORBENT CORE

(75) Inventors: Takuya Kouta, Tochigi (JP); Masashi Kawazoe, Tochigi (JP); Takeshi Miyamura, Tochigi (JP)

(73) Assignee: Kao Corporation, Tokyo (JP)

( * ) Notice: Subject to any disclaimer, the term of this patent is extended or adjusted under 35 U.S.C. 154(b) by 347 days.

(21) Appl. No.: 12/678,117

(22) PCT Filed: Nov. 25, 2008

(86) PCT No.: PCT/JP2008/071319
§ 371 (c)(1),
(2), (4) Date: Aug. 6, 2010

(87) PCT Pub. No.: WO2009/072414
PCT Pub. Date: Jun. 11, 2009

(65) Prior Publication Data
US 2010/0312217 A1 Dec. 9, 2010

(30) Foreign Application Priority Data
Dec. 6, 2007 (JP) .................................. 2007-316239

(51) Int. Cl.
*A61F 13/15* (2006.01)

(52) U.S. Cl.
USPC ............ 604/385.16; 604/385.22; 604/385.24; 604/379; 604/378; 604/385.101; 604/380

(58) Field of Classification Search
USPC .................. 604/385.16, 385.22, 385.24, 379, 604/378, 385.101, 380
See application file for complete search history.

(56) References Cited

U.S. PATENT DOCUMENTS

| | | | |
|---|---|---|---|
| 6,183,458 B1 * | 2/2001 | Ahlstrand et al. | ....... 604/385.19 |
| 2004/0243081 A1 | 12/2004 | Suzuki et al. | |

FOREIGN PATENT DOCUMENTS

| | | |
|---|---|---|
| EP | 0591647 A2 | 4/1994 |
| JP | 53-88582 | 7/1978 |
| JP | 2001-46435 A | 7/1978 |
| JP | 6-90977 A | 4/1994 |
| JP | 10-508528 A | 8/1998 |
| JP | 2001-214399 A | 8/2001 |
| JP | 2003-70843 A | 3/2003 |
| JP | 2003-103677 A | 4/2003 |
| WO | WO 91/09581 A1 | 7/1991 |
| WO | WO 96/07476 A1 | 3/1996 |

OTHER PUBLICATIONS

Chinese Office Action, dated May 31, 2012, for Chinese Application No. 200880117613.6, along with English translation.
English translation of International Preliminary Report on Patentability (Form PCT/IB/336 and 373) and of Written Opinion of the International Searching Authority mailed on Aug. 19, 2010 in PCT/JP2008/071319.
Machine-Generated Translation for JP-53-88582-U, published Jul. 20, 1978.

(Continued)

*Primary Examiner* — Jacqueline F. Stephens
(74) *Attorney, Agent, or Firm* — Birch, Stewart, Kolasch & Birch, LLP

(57) ABSTRACT

A stretchable absorbent core (10) includes a stretchable base sheet (20), and a plurality of separate and independent absorbers (30) disposed at least on one side of the base sheet (20). The absorbers (30) are fixed to the base sheet (20) through respective fixing points (33) in such a design that the shape of each absorber is not deformed upon stretch of the base sheet (20). The stretchable absorbent core (10) exhibits stretchability between the fixing points (33). It is preferable that the stretchable absorbent core (10) does not exhibit stretchability at the fixing points (33).

12 Claims, 6 Drawing Sheets

OTHER PUBLICATIONS

Notice of Rejection for corresponding Japanese Patent Application No. 2007-316239, mailed Aug. 7, 2012.

Notice of Rejection for corresponding Japanese Patent Application No. 2007-316239, mailed Oct. 30, 2012.

* cited by examiner

STRETCHABLE ABSORBENT CORE

TECHNICAL FIELD

The present invention relates to a stretchable absorbent core. The stretchable absorbent core of the invention is suitably used as a constituent core for absorbent articles such as sanitary napkins and disposable diapers.

BACKGROUND ART

Absorbent articles having stretchable absorbent core are known in the art. Patent Document 1, for example, discloses a stretchable sheet-like absorbent core that has a conjugate sheet consisting of an elastic sheet 11 and a nonwoven fabric 12 bonded to the elastic sheet 11. The nonwoven fabric 12 of the conjugate sheet is joined to the elastic sheet 11 continuously in a first direction, but joined in a discontinuous manner in a second direction orthogonal to the first direction such that the nonwoven fabric 12 has some allowance with respect to the elastic sheet 11. Joining the sheets in this way forms channels extending in the first direction and parallel to one another. Rod-like absorbers 15 are respectively placed in those channels. Extending this sheet-like absorbent core stretches and flattens out the channels formed by the nonwoven fabric 12. The shapes of the channels thus deform depending on the stretch state of the sheet-like absorbent core, which causes variation in the distance between the nonwoven fabric 12 and each of the absorbers 15. This means that the absorbency of the sheet-like absorbent core varies depending on the degree of stretch thereof. That is, stretch of the sheet-like absorbent core due to a wearer's movement etc. causes variation in its absorbency.

Patent Document 2 discloses a resilient body including two thin layers 1 and 6, and material bodies 4 disposed between the two thin layers 1 and 6 according to a given pattern, at least one of the two layers being woven by elastic threads for providing stretchability. The two thin layers 1 and 6 are attached mutually spaced from one another in their stretched state. Similar to the sheet-like absorbent core disclosed in Patent Document 1, the material bodies 4 in the resilient body deform depending on the degree of stretch of the resilient body, which results in that stretch of the sheet-like absorbent core due to a wearer's movement etc. causes variation in its absorbency.

Aside from the techniques disclosed in Patent Documents 1 and 2, Patent Document 3 discloses an absorbent core of an absorbent article that consists of a laminate of a nonwoven fabric layer and a fibrous web layer. The laminate includes first network regions that are thin and have high density, and second network regions that are thick and have a lower density than the first network regions. The surface of the fibrous web layer is bulky and has projections and depressions. The first network regions are arranged in the form of bands intersecting one another, whereas the second network regions are provided as partitioned layers surrounded by the first network regions. This laminate absorbent core, however, has no stretchability, and thus will not easily conform to a wearer's movement, leading to poor adaptability to the body.

Patent Document 1: Japanese Patent Laid Open JP-A-6-90977
Patent Document 2: International Publication WO 91/09581
Patent Document 3: Japanese Patent Laid Open JP-A-2003-103677

DISCLOSURE OF THE INVENTION

The present invention provides a stretchable absorbent core including a stretchable base sheet, and a plurality of separate and independent absorbers disposed at least on one side of the base sheet.

The present invention also provides a stretchable absorbent core in which the absorbers are fixed to the base sheet through respective fixing points in such a design that the shape of each of the absorbers is not deformed upon stretch of the base sheet, and stretchability is exhibited between the fixing points.

The present invention also provides an absorbent article including such a stretchable absorbent core.

DETAILED DESCRIPTION OF THE INVENTION

Figure 1:
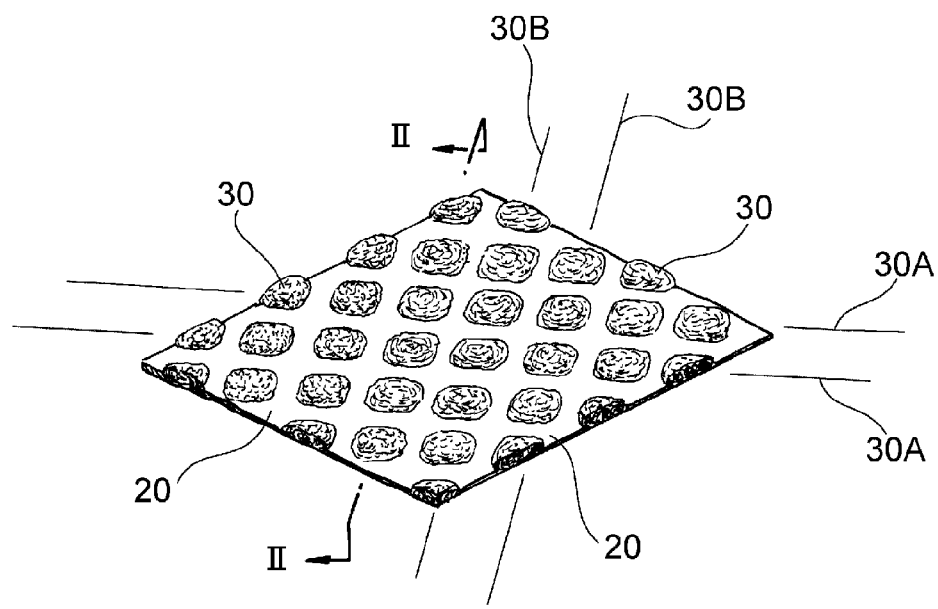
FIG. 1 is a perspective showing an embodiment of a stretchable absorbent core according to the invention.
Figure 2:
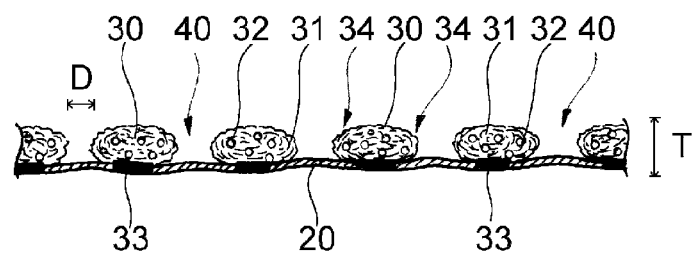
FIG. 2 is a cross-sectional view taken along line II-II of FIG. 1.

The present invention is described below according to preferred embodiments thereof with reference to the drawings. FIG. 1 shows a perspective of an embodiment of the invention. FIG. 2 is a cross-sectional view taken along line II-II of FIG. 1. A stretchable absorbent core 10 of this embodiment is suited for use particularly as a core constituting an absorbent article such as a sanitary napkin or a disposable diaper, and is used for absorbing liquid. The stretchable absorbent core 10 includes a base sheet 20 and a plurality of absorbers 30 disposed on one side of the base sheet.

The base sheet 20 is a sheet-like material that has stretch property in at least one direction within its plane. The base sheet 20 serves as a part for rendering the absorbent core 10 stretchable. The term "stretchable" refers to a property that allows an element to be extended and to be contracted by canceling the extended state. The direction in which the base sheet 20 extends and contracts within a plane depends, for example, on how the base sheet 20 is produced. Preferably, the base sheet 20 is stretchable in two directions—i.e., a certain direction within a plane and a direction orthogonal thereto—, and more preferably, stretchable in all directions within a plane.

The base sheet 20 may either be permeable to liquid, or impermeable or hardly permeable to liquid. The property of the base sheet 20 regarding liquid permeability can be selected as appropriate depending on the intended use of the stretchable absorbent core 10. The liquid permeability of the base sheet 20 is determined, for example, according to the type of constituent material used, whether a wettability improver is applied or not, and how the base sheet 20 is produced.

The base sheet 20 may be a single-layer sheet or a multi-layer laminate sheet in which a plurality of sheets are joined together.

The absorbers 30 disposed on one side of the base sheet 20 are parts capable of absorbing and retaining liquid. There is no particular limitation to the type of material constituting the absorbers 30, as long as they are capable of absorbing and retaining liquid. As shown, for example, in FIG. 2, the absorber 30 is made of a mixture of a fibrous material 31 and high-absorbent polymer 32. In this example, the high-absorbent polymer 32 is retained within the fibrous material 31.

When viewed from above, the absorber 30 has the shape of a circle or a rectangle whose corners are rounded and whose sides each take the form of a gentle curve slightly convex outward. The plan-view shape of the absorber 30, however, is not limited to the above. For example, the plan-view shape of the absorber 30 may be a square, a rectangle, or a rhombus. Further, two or more of these shapes may be used in combination.

The absorbers 30 are disposed on the base sheet 20 across the planar direction thereof according to a regular, scattered pattern. More specifically, the absorbers 30 are disposed so as to be lined up in a plurality of first rows 30A and a plurality of second rows 30B intersecting with the first rows 30A. The surface of the base sheet 20 is exposed between adjacent absorbers 30. Thus, spaces 40 are formed between adjacent absorbers 30, each space 40 including the exposed section of the base sheet 20. Where the stretchable absorbent core 10 of the present embodiment is used for example as an absorbent core of an absorbent article, the spaces 40 are designed to have a capacity, width, and/or height allowing permeation of liquid having passed through the topsheet as well as flow of liquid in the stretchable absorbent core 10.

The absorbers 30 are fixed to the base sheet 20 through respective fixing points 33 in such a design that the shape of each absorber 30 is not deformed upon stretch of the base sheet 20. For convenience' sake, the fixing points 33 are shown with bold lines in FIG. 2. In order to keep the shape of each absorber 30 from deforming upon stretch of the base sheet 20, it is advantageous that the stretchable absorbent core 10 does not exhibit stretchability at the fixing points 33. Due to the fixing points 33 not exhibiting stretchability, the base sheet 20 neither extends nor contracts at the fixing points 33, even when the base sheet 20 as a whole is extended or contracted. Thus, the absorbers 30 fixed to the base sheet 20 respectively through the fixing points 33 are not influenced by the stretch of the base sheet 20, which keeps the shape of each absorber from deforming upon stretch of the base sheet 20. Because the absorbers 30 do not deform in shape, the absorbency hardly changes even upon stretch of the stretchable absorbent core 10. Therefore, an absorbent article including the stretchable absorbent core 10 of the present embodiment exhibits stable absorbency throughout the period worn.

In order to keep the stretchable absorbent core 10 from exhibiting stretchability at the fixing points 33, the stretchability of the base sheet 20 may be eliminated, for example, by forming the fixing points 33 through ultrasonic embossing. Forming the fixing points 33 with an adhesive such as a hot melt adhesive also allows the stretchability of the base sheet 20 to be eliminated.

Figure 3:
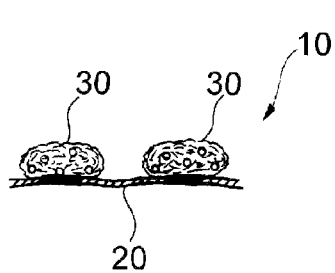
FIGS. 3(a) and 3(b) are schematic diagrams showing stretch states of the stretchable absorbent core of FIG. 1.
Figure 3:
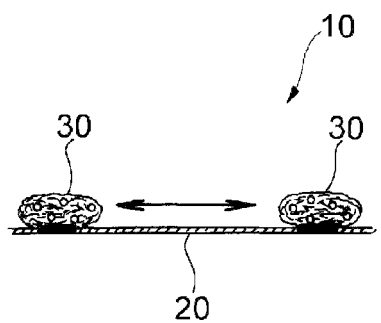

As described above, the stretchable absorbent core 10 of the present embodiment does not exhibit stretchability at the fixing points 33. In other words, only sections between the fixing points 33 exhibit stretchability in the stretchable absorbent core 10. That is, when the stretchable absorbent core 10 in its natural state (relaxed state) as shown in FIG. 3(a) is extended in its planar direction, only the sections between the fixing points 33 extend as shown in FIG. 3(b). Here, the absorbers 30 do not deform in shape. When the extended state of the stretchable absorbent core 10, which is in its extended state as shown in FIG. 3(b), is canceled, only the sections between the fixing points 33 contract, causing no deformation in the shape of the absorbers 30. Having such a stretchable property, the stretchable absorbent core 10 is superior in adaptability to a wearer's body and conformability to a wearer's movement.

Figure 4:
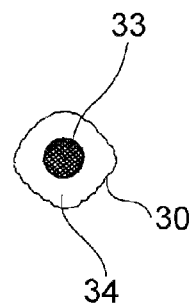
FIG. 4 is an explanatory diagram showing a positional relationship between an absorber and a fixing point when viewing the stretchable absorbent core of FIG. 1 from above.

FIG. 4 shows a positional relationship between the absorber 30 and the fixing point 33 when the stretchable absorbent core 10 is viewed from above. As is clearly seen from the figure, the contour of the fixing point 33 is encompassed within the contour of the absorber 30 when viewed from above. Also, as is clearly seen from FIG. 2, the absorbers 30 are located on the respective fixing points 33. Thus, the absorber 30 is shaped so that it has an overhanging projection 34 (hereinafter referred to as an overhang 34) outwardly projecting from the fixing point 33 in the planar direction. The overhang 34 may be spaced from the base sheet 20, or the bottom surface of the overhang 34 may be in contact with the base sheet 20. In either case, however, the absorber 30 is not fixed to the base sheet 20 at its overhang 34. Providing an overhang 34 to each absorber 30 minimizes the area of the base sheet 20 in which stretchability is lost due to formation of the fixing points 33 to thereby allow the base sheet 20 to maintain satisfactory stretchability, and also maximizes the total area of the absorbers 30 to thereby allow the absorbency of the stretchable absorbent core 10 to be improved. Maintaining satisfactory stretchability of the base sheet 20 leads to improved adaptability and conformability to the wearer's body. Maximizing the total area of the absorbers 30 keeps the distance between adjacent absorbers 30 from increasing so much even when the stretchable absorbent core 10 is extended, which leads to the effect of suppressing reduction in absorbency.

Note that, although the fixing point 33 has a circular plan-view shape in FIG. 4, the plan-view shape thereof is not limited thereto. For example, the plan-view shape of the fixing point 33 may be a square, a rectangle, or a rhombus. Further, two or more of these shapes may be used in combination. Furthermore, the combination of the shapes of the fixing point 33 and the absorber 30 as viewed from above is not particularly limited to that shown in FIG. 4.

From the standpoint of achieving both stretchability and satisfactory absorbency of the stretchable absorbent core 10, it is preferable that the plan-view area of each absorber 30, in its natural state (relaxed state), is 10 to 900 $mm^2$, and more preferably 50 to 450 $mm^2$. Further, from the standpoint of improving the wearer's comfort of the absorbent article having the stretchable absorbent core 10 and the standpoint of reducing the rigidity of the stretchable absorbent core 10 to make the absorbent article having the stretchable absorbent core 10 adapt to the wearer's body, it is preferable that the thickness T (see FIG. 2) of the stretchable absorbent core 10 where the absorbers 30 exist—i.e., the sum of the thickness of the absorber 30 and the thickness of the base sheet 20—is 1 to 10 mm, and more preferably 1.2 to 5 mm. The area and thickness T of the absorber 10 can be adjusted by controlling the conditions for producing the stretchable absorbent core 10, which are described further below.

Further, from the standpoint of providing sufficient strength so that the absorber 30 does not fall off due to stretch of the base sheet 20, it is preferable that the area of each fixing point 33 for fixing the absorber 30 to the base sheet 20 is 1 to 100 mm$^2$, and more preferably 5 to 50 mm$^2$, provided that the area of the fixing point is smaller than that of the absorber 30 when viewed from above. Furthermore, from the standpoint of minimizing the area of the base sheet 20 in which stretchability is lost to minimize impairment of stretchability of the base sheet 20, it is preferable that the total sum of the area of the fixing points 33, as viewed from above, is 5% to 95%, and more preferably 20% to 70%, with respect to the area of the base sheet 20.

The distance D (see FIG. 2) between adjacent absorbers 30 has an influence on the capacity of the space 40 and thus the flowability of liquid through the space 40. From this standpoint, it is preferable that the distance D in the natural state (relaxed state) is 0.2 to 5 mm, and more preferably 0.5 to 3 mm. The distance D can be adjusted by controlling the conditions for producing the stretchable absorbent core 10, which are described further below. Note that, if there are a plurality of other absorbers 30 around a certain absorber 30 and the distance D between that certain absorber 30 and another one of the absorbers 30 differs depending on the other absorber 30, then the minimum distance D is regarded as the "distance between adjacent absorbers 30".

The material constituting the absorber 30 is not particularly limited, and fibrous materials, porous elements, and combinations thereof may be used. Examples of fibrous materials that may be used include: natural fibers such as wood pulp, cotton, and hemp; single fibers made of synthetic resin including e.g. polyolefin-based resin such as polyethylene and polypropylene, polyester-based resin such as polyethylene terephthalate, and polyvinyl alcohol resin; conjugate fibers including two or more types of these resins; and semi-synthetic fibers such as acetate and rayon. In cases where a fiber made of synthetic resin is to be used, it may be a heat-shrinkable fiber that deforms by heat. For example, it is possible to employ a fiber whose fineness increases but whose fiber length decreases by heat, or a fiber whose fineness hardly changes by heat but whose apparent occupied length (the apparent length that the fiber occupies) decreases due to it deforming into a coil. Examples of porous elements that may be used include sponge, nonwoven fabrics, and an aggregate of high-absorbent polymer (i.e., an aggregate of high-absorbent polymer and fiber).

Preferable polymers for the high-absorbent polymer 32 contained in the absorber 30 include those that can absorb and retain body fluid of an amount five times or more of its own weight and that can gel. There is no particularly preferable shape therefor, and the polymer may be spherical, clump-like, botryoidal, powdered, or fibrous. Particulate polymers having a size of 1 to 1000 μm, and more preferably 10 to 500 μm, are preferred. Examples of such high-absorbent polymers may include starch, cross-linked carboxyl methyl cellulose, polymers or copolymers of acrylic acid or alkali metal salts thereof, polyacrylic acid or salts thereof, and graft polymers of polyacrylic acid salts. Preferable polyacrylic acid salts that can be used are sodium salts. It is also possible to preferably use copolymers in which a comonomer, such as maleic acid, itaconic acid, acrylamide, 2-acrylamido-2-methylpropane sulfonic acid, 2-(meth)acryloyl ethane sulfonic acid, 2-hydroxyethyl (meth)acrylate, or styrene sulfonic acid, is copolymerized with acrylic acid within a range that does not deteriorate the performance of the high-absorbent polymer.

In the present invention, it is not essential for the absorber 30 to include the high-absorbent polymer 32. However, in cases where the absorber 30 includes the high-absorbent polymer 32, the ratio of the high-absorbent polymer 32 with respect to the weight of the absorber 30 is preferably 5% to 95% by weight. In cases where the stretchable absorbent core 10 is to be used as an absorbent core of a sanitary napkin or an article used for absorbing a small amount of excreted fluid such as light incontinence, the ratio of the high-absorbent polymer 32 with respect to the weight of the absorber 30 is preferably 10% to 30% by weight. In cases where the stretchable absorbent core 10 is to be used as an absorbent core of an article used for absorbing a large amount of excreted fluid, such as a disposable diaper, the ratio of the high-absorbent polymer 32 with respect to the weight of the absorber 30 is preferably 50% to 80% by weight.

From the standpoint of exhibiting stable absorbency even upon stretch of the base sheet 20, it is preferable that the amount of 0.9-percent-by-weight sodium chloride solution the stretchable absorbent core 10 can retain (i.e., the retention amount of the stretchable absorbent core 10) is equal to or above 0.1 g/g, and more preferably equal to or above 1 g/g, regardless of whether the absorbers 30 include the high-absorbent polymer or not. In order to achieve such a retention amount, it is advantageous to use, in combination, a highly-hydrophilic fiber having a strong capillary force (such as pulp or rayon), a synthetic fiber that does not sink down when wet (i.e., that is neither plasticized nor reduced in wet strength), and a high-absorbent polymer, as the material constituting the absorber 30.

The above-described retention amount is measured as follows. Measurement is carried out at 25±2° C. and at a relative humidity of 50% RH±5%. First, an evaluation sample is prepared by cutting out a stretchable absorbent core into a square 50 mm long and 50 mm wide, and the weight ($M_0$) of the evaluation sample is measured. The evaluation sample is then placed in a 500 ml beaker containing 400 ml of a 0.9-percent-by-weight sodium chloride solution and immersed therein for one hour. After an hour, the evaluation sample is taken out from the beaker, and is placed on an acrylic plate inclined at 45 degrees and left thereon for ten minutes to drain. The weight ($M_1$) after draining is then measured. The retention amount is calculated from the following equation, and an average value for n=5 (i.e., an average value for five evaluation samples) is considered as the retention amount of the stretchable absorbent core with respect to the sodium chloride solution.

$$\text{Retention amount (g/g)} = (M_1 - M_0)/(M_0)$$

Any kind of sheet having stretchability can be used, without particular limitation, as the base sheet 20 onto which the absorbers 30 are fixed. Examples of such sheets may include: nonwoven fabrics that include, as a constituent, fiber including elastic resin (i.e., elastic nonwoven fabrics); films including elastic resin (i.e., elastic films); and elastic porous elements made of elastic resin having a structure formed into a three-dimensional network by means of foaming etc. Any type of elastic nonwoven fabric, elastic film, or elastic porous element known in the present technical field can be used. It is preferable that the basis weight of the base sheet 20 is 5 to 50 g/m², and more preferably 10 to 30 g/m².

It is preferable that the degree of stretchability of the base sheet 20 is 60% or above, and more preferably 80% or above, in stretch ratio which is measured as follows, from the standpoint of providing particularly favorable adaptability to a wearer's body and conformability to a wearer's movement. The stretch ratio is measured as follows. Measurement is carried out using a tension/compression tester RTC-1210A (supplied by Orientec Co., Ltd.) in the "tension mode". First, a measurement piece is sampled by cutting the base sheet 20 into a strip 25 mm wide and 150 mm long. The measurement piece is set between air chucks that are installed in the tension/compression tester at an initial sample length (chuck-to-chuck distance) of 100 mm, and the piece is extended by raising the chuck mounted to the load cell (rated output of 5 kg) of the tension/compression tester at a speed of 300 mm/min. When the measurement piece has been extended by a length 50% of the initial sample length, i.e., by 50 mm, the movement direction of the chuck is reversed, and the chuck is lowered at a speed of 300 mm/min and returned to the position of the initial sample length. During this operation, the relationship between the load detected by the load cell and the extension of the measurement piece is recorded in a chart, and the stretch ratio is obtained from the following equation (1) based on the chart.

$$\text{Stretch ratio} = \text{Recovery extension}/\text{Maximum extension length } (=50 \text{ mm}) \quad (1)$$

The "recovery extension" is defined as the distance the chuck has moved from the maximum extension length (=50 mm) at the time the load first becomes zero after starting to lower the chuck from the maximum extension length. Note that in cases where the measurement piece cannot extend up to the above-described size, measurement is carried out according to the following method.

<Measurement Piece>

Assuming that the length of the sheet in the chuck-to-chuck direction is L mm, the length of a section that is held is S mm, and the width of the sheet is C mm, a measurement piece is sampled by cutting the base sheet into a specimen (L+2S) mm long×C mm wide in such a manner that the length ratio L:C becomes 3:5.

<Test>

The specimen is set to the tension/compression tester at a chuck-to-chuck distance of L, and the chuck is raised at a speed of 100×(L/30) mm/min until the measurement piece is extended by a length 50% of the initial sample length. The movement direction of the chuck is then reversed, and the chuck is lowered at a speed of 100×(L/30) mm/min and returned to the position of the initial sample length. Calculation is made according to the following equation (2):

$$\text{Stretch ratio} = \text{Recovery extension}/\text{Maximum extension length } (=L/2 \text{ mm}) \quad (2)$$

Figure 5:
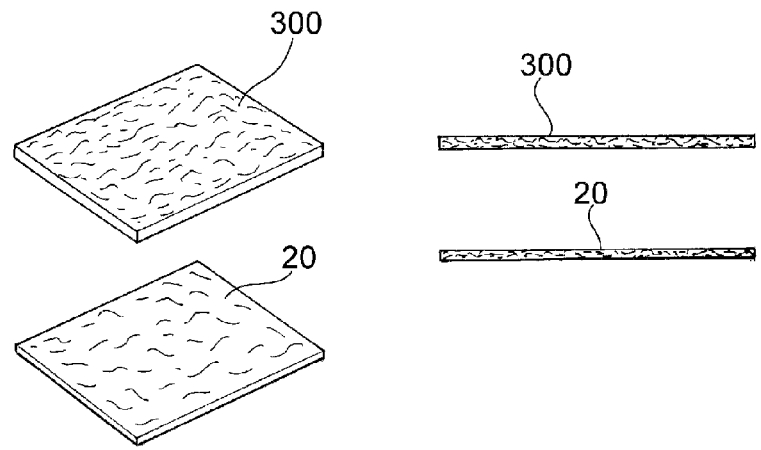
FIGS. 5(a) to 5(c) are process flow diagrams sequentially showing a process for producing the stretchable absorbent core of FIG. 1.
Figure 5:
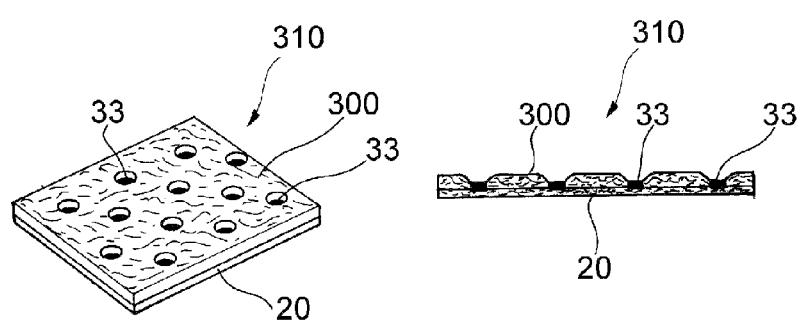
Figure 5:
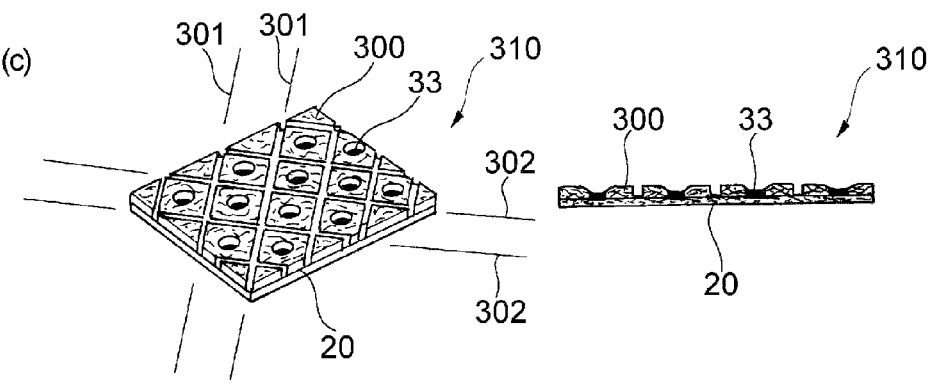
Figure 8:
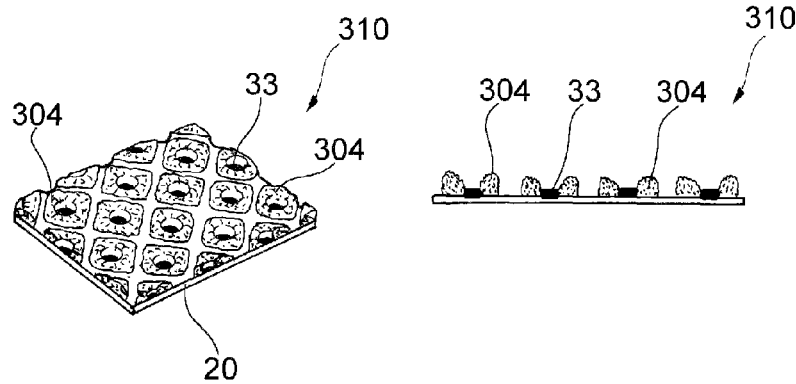
FIGS. 8(a) and 8(b) are process flow diagrams sequentially showing a process for producing the stretchable absorbent core of FIG. 1 following the step of FIG. 5(c).
Figure 8:
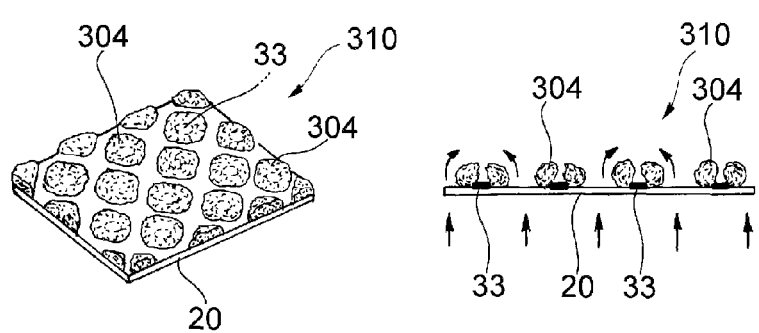

Now, a preferable process for producing the stretchable absorbent core 10 of the present embodiment is described with reference to FIGS. 5 to 8. In order to facilitate understanding of the process, FIG. 5 and FIG. 8 show the components in each production step using both perspectives and cross-sectional views. First, as shown in FIG. 5(a), a base sheet 20 and a fibrous sheet 300 are prepared. A sheet of the above-described type is used as the base sheet 20. A heat-shrinkable sheet including a heat-shrinkable fiber is used as the fibrous sheet 300. The fibrous sheet 300 may further include, as necessary, rayon, synthetic fibers that are not heat shrinkable, and/or absorbent fibers. A fibrous web may be used as the fibrous sheet 300. A "fibrous web" is an aggregation of fiber in which the constituent fibers are entangled together loosely to such a degree that the fibers cannot be kept in a sheet-like structure. In cases where high stability is required for carrying the fibrous sheet 300, a nonwoven fabric may be used as the fibrous sheet 300 instead of a fibrous web. When using a nonwoven fabric, it is preferable to use one that is made using non-thermal means, such as ultrasonic embossing, binders, or needle-punching, in order to keep the heat-shrinkable fiber from shrinking during the step of producing the nonwoven fabric. It is, however, possible to use a nonwoven fabric made using thermal means, such as the air-through process, as long as the obtained nonwoven fabric exhibits heat shrinkability.

After the fibrous sheet 300 is placed on one side of the base sheet 20, the sheets are partially joined together to form a plurality of fixing points 33 as shown in FIG. 5(b), thereby obtaining a laminate 310. In forming the fixing points 33, it is preferable to use non-thermal means, such as ultrasonic embossing or adhesives. It is, however, possible to use thermal means, such as hot embossing or hot melt adhesives, as long as the fibrous sheet 300 having the fixing points 33 formed thereon exhibits heat shrinkability. That is, thermal means may be used on the condition that the heat shrinkability of the fibrous sheet 300 is not inhibited. In forming the fixing points 33, it is important that the stretchability of the base sheet 20 is eliminated at the fixing points 33 that are formed so that they do not exhibit stretchability. In cases where ultrasonic embossing is adopted as the joining means for eliminating the stretchability of the base sheet 20 at the fixing points 33, the elasticity may be eliminated by applying energy to the base sheet 20 and thereby melting and setting the elastic resin included in the base sheet 20 to turn the base sheet 20 at the fixing points into a film. In cases where an adhesive is used as the joining means, it is possible to fill the space between the base sheet 20 and the fibrous sheet 300 with the adhesive and bond the two sheets together so that the bonded sections exhibit such a strength that the two sheets do not fall apart. In this way, the sections hardened by the adhesive lose stretchability.

Figure 6:
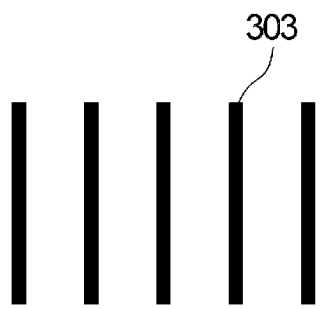
FIG. 6 is a diagram showing a pattern according to which fibers constituting a fibrous sheet in a laminate are cut.
Figure 7:
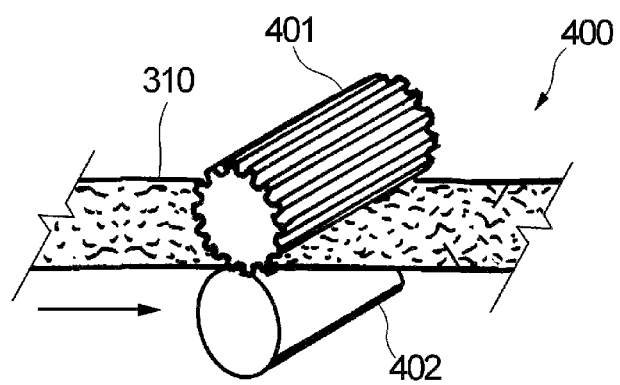
FIG. 7(a) is a schematic diagram showing a device for cutting the fibers constituting the fibrous sheet in the laminate.
FIGS. 7(b) and 7(c) are schematic diagrams respectively showing different shapes of a first roll in the device shown in FIG. 7(a).
Figure 7:
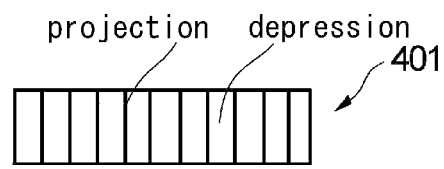
Figure 7:
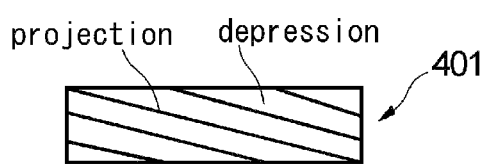

Then, high-absorbent polymer is sprinkled onto the fibrous sheet 300 as necessary (not shown). Thereafter, the fibers constituting the fibrous sheet 300 are cut between adjacent fixing points 33, as shown in FIG. 5(c). Here, it is important that only the fibers constituting the fibrous sheet 300 are cut, and not the base sheet 20. In the present embodiment, only the fibers constituting the fibrous sheet 300 are cut along a multitude of first cut lines 301 extending in a straight line and parallel to one another and a multitude of second cut lines 302 intersecting with the first cut lines 301 and extending in a straight line and parallel to one another. The cutting pattern, however, is not limited to the above, and for example, the fibrous sheet may be cut in such a manner that the cut sections 303 extend in a multitude of straight lines parallel to one another, as shown in FIG. 6. Further, in place of the straight-line cutting pattern shown in FIG. 6, it is possible to adopt various cutting patterns, such as smooth wavy lines shaped like a sinusoidal wave or angled wavy lines.

In order to cut the fibers constituting the fibrous sheet 300 of the laminate 310, it is possible, for example, to use a cutting device 400 including a first roll 401 and a second roll 402 as shown in FIG. 7(a). The first roll 401 is a pattern-indented roll (roll with grooved blades) in which axially-extending depressions and projections are alternately arranged along the rotating direction of the roll. The tip end of each projection forms a sharp cutting blade. The second roll 402 is a metal or rubber roll having a smooth surface. The laminate 310 is passed between the rolls in such a manner that the fibrous sheet 300 of the laminate 310 is faced toward the first roll 401, and in this way, only the fibers constituting the fibrous sheet 300 of the laminate 310 are cut. The cut lines 301 and 302 of the pattern shown in FIG. 5(c) can be formed by passing the laminate 310 between the rolls 401 and 402 at least twice while changing the angle at which the laminate 310 is passed between the rolls 401 and 402 every time the laminate is passed. Note that the fibrous sheet 300 may be cut according to various patterns by using, alone or in combination, rolls having such patterns as those shown in FIGS. 7(b) and 7(c) as the first roll 401.

After cutting the fibers constituting the fibrous sheet 300, heat is applied to the laminate 310 to cause the heat-shrinkable fiber contained in the fibrous sheet 300 to shrink. The temperature of the applied heat is set equal to or above the shrink-start temperature of the heat-shrinkable fiber and below the melt temperature. Through heat shrinking, the fibers constituting the fibrous sheet 300 gather toward each fixing point 33 as well as rise up in the thickness direction as shown in FIG. 8(a), thereby forming annular raised sections 304. Each annular raised section 304 is located around a fixing point 33 so as to surround that fixing point 33. Controlling the extent to which the heat-shrinkable fiber is shrunk allows the distance D between adjacent absorbers 30 in the intended stretchable absorbent core 10 to take a desired value.

Then, as shown in FIG. 8(b), air is blown from the side of the base sheet 20 in the laminate 310. The blown air passes through the base sheet 20 and uplifts the fibers constituting the annular raised sections 304 around the respective fixing points 33. With this uplift, the fibers constituting the annular raised sections 304 thermally shrink and gather onto the respective fixing points 33, thus forming raised sections on the respective fixing points 33. These raised sections constitute the absorbers 30 in the intended stretchable absorbent core 10. In this way, the intended stretchable absorbent core 10 is made.

By blowing air as shown in FIG. 8(b) while causing the heat shrinking as shown in FIG. 8(a), the heat-shrinkable fiber is entangled with the fibers constituting the fibrous sheet 300 while shrinking, and in this way, the raised sections are successively formed on the respective fixing points 33.

Note that the operation shown in FIG. 8(b) is effective in cases where the base sheet 20 has sufficient breathability. In cases where the base sheet 20 has no breathability or extremely poor breathability, it is preferable to blow air in the transverse direction (horizontal direction) onto the fibers constituting the fibrous sheet 300 or the annular raised sections 304, in place of the operation shown in FIG. 8(b). In that case, the raised sections can successively be formed on the respective fixing points 33 by blowing air in two orthogonal directions.

The following describes another way of producing the stretchable absorbent core 10. First, a multitude of cut sections consisting of through holes or incisions are formed in advance in the fibrous sheet 300 before being joined to the base sheet 20. Note that the cut sections are formed to have such a size and/or shape and/or arrangement pattern that allows the fibrous sheet 300 to maintain its form as a sheet and that allows the fibrous sheet 300 to separate into a multitude of cut pieces at the cut sections when the fibrous sheet 300 is extended. Then, the fibrous sheet 300 and the base sheet 20 are joined together. Following this, the base sheet 20 is extended, which in turn causes the fibrous sheet 300 to separate into a multitude of cut pieces that are fixed to the base sheet 20 respectively at the positions of the fixing points 33.

This state corresponds to the state shown in FIG. 5(c) described above. Thereafter, the operations shown in FIGS. 8(a) and 8(b) are carried out.

The stretchable absorbent core 10 obtained in this way is preferably used as a constituent core of various absorbent articles such as sanitary napkins and disposable diapers. A typical absorbent article has a topsheet, a backsheet, and a liquid-retainable absorbent core disposed between the two sheets. A pair of three-dimensional guards may be disposed on the right and left sides on the topsheet. In an absorbent article having such a structure, the stretchable absorbent core 10 is used as the liquid-retainable absorbent core disposed between the topsheet and the backsheet or as the three-dimensional guard.

Figure 9:
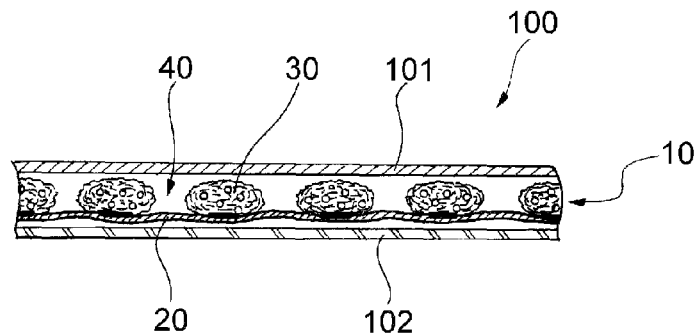
FIG. 9 is a schematic diagram showing a vertical cross-sectional structure of an absorbent article having the stretchable absorbent core of FIG. 1.

FIG. 9 schematically shows a cross-sectional structure of an absorbent article having the stretchable absorbent core 10, the cross section being taken along the width direction in the lengthwise middle region. Although not shown in the drawings, the cross-sectional structure taken along the length direction in the widthwise middle region is substantially the same as FIG. 9. The absorbent article 100 has a topsheet 101 that faces the wearer's skin and a backsheet 102 that faces outward. The stretchable absorbent core 10 is disposed between the sheets 101 and 102. The stretchable absorbent core 10 is disposed in such a manner that the side with the absorbers 30 faces the topsheet 101 and the side without the absorbers 30 faces the backsheet 102. The side of the stretchable absorbent core 10 without the absorbers 30 may be joined to the backsheet 102, but does not necessarily have to be joined thereto. As regards the side of the stretchable absorbent core 10 with the absorbers 30, the top surface of the absorbers 30 may be joined to the topsheet 101, but does not necessarily have to be joined thereto.

There is no particular limitation to the material constituting the topsheet 101 and the backsheet 102. However, taking account of the fact that the absorbent core 10 is stretchable, it is preferable that the topsheet 101 and the backsheet 102 also are stretchable or deformable. In this way, the absorbent article 100 as a whole will exhibit stretchability. As a stretchable topsheet 101, it is possible to use, for example, a nonwoven fabric that includes, as its constituent, fibers including elastic resin, or a perforated film including elastic resin. As a deformable topsheet 101, it is possible to use, for example, a projecting-and-depressed sheet having a wavy cross section, a nonwoven fabric made by needle-punching and having a multitude of holes, or a pleated nonwoven fabric. Such nonwoven fabrics and films are permeable to liquid. As a stretchable backsheet 102, it is possible to use a film including elastic resin, the film being impermeable or hardly permeable to liquid. The film may be moisture permeable.

In the absorbent article 100 shown in FIG. 9, fluid that is excreted onto the topsheet 101 is quickly drawn into the absorbers 30 which are in contact with the topsheet 101. The fluid drawn into the absorbers 30 is guided along the spaces 40 existing among the absorbers 30 and promptly diffused in the planar direction of the absorbent core 10. The spaces 40 in the absorbent core 10 of the present embodiment are formed extending in both the length direction and the width direction of the absorbent article 100, and thus, the fluid is guided in every direction of the absorbent article 100. In cases where the base sheet 20 is made of a liquid-impermeable sheet (such as a film) in order to improve the fluid diffusibility in the spaces 40, it is preferable to make the sheet slightly water-repellent. In cases where the base sheet 20 is made of a nonwoven fabric, it is preferable to orient the fluid-diffusion direction in a particular direction by controlling the orientation of the fiber constituting the nonwoven fabric. In this case, it is preferable that the constituent fiber is water-repellent. The fiber constituting the nonwoven fabric, however, may be hydrophilic, in which case the base sheet 20 at positions corresponding to the spaces 40 mainly absorbs the fluid, rather than diffusing the fluid at the spaces 40. Such a fluid absorption/diffusion mechanism suppresses fluid leakage.

Aside from the absorbent article 100 shown in FIG. 9, in cases where the stretchable absorbent core 10 of the present embodiment is to be used as a pair of three-dimensional guards located at the right and left sides of the absorbent article, the stretchable absorbent cores 10 are disposed with the absorbers 30 of the respective absorbent cores 10 facing one another.

Figure 10:
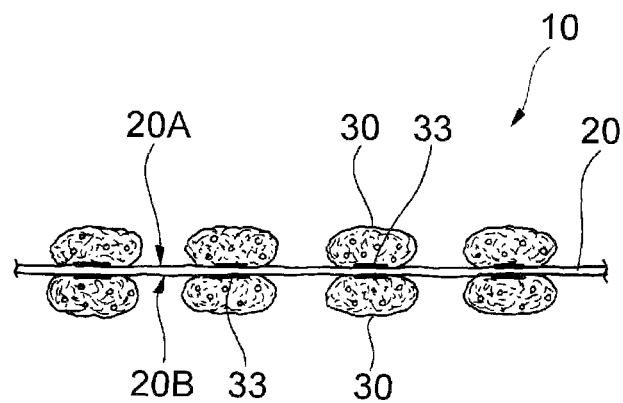
FIGS. 10(a) and 10(b) are vertical cross-sectional views respectively showing other embodiments of a stretchable absorbent core according to the present invention, each corresponding to FIG. 2.
Figure 10:
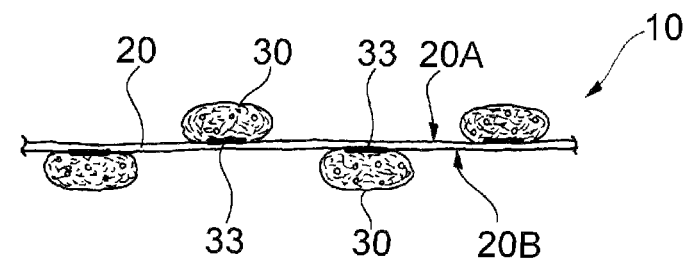
Figure 11:
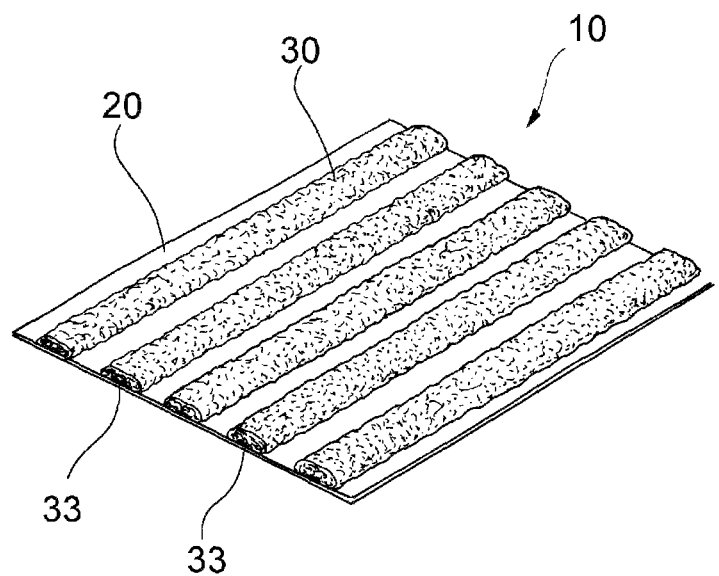
FIG. 11 is a perspective showing another embodiment of a stretchable absorbent core according to the present invention, which corresponds to FIG. 1.

Next, other embodiments of the present invention are described with reference to FIGS. 10 and 11. As for these embodiments, only features that differ from those of the above-described embodiment are described below, and the explanation on the above-described embodiment applies as appropriate to the features in common. In FIGS. 10 and 11, the same components as those in FIGS. 1 to 9 are accompanied with the same reference numerals.

In a stretchable absorbent core 10 according to the embodiment shown in FIG. 10(a), the absorbers 30 are formed on both sides of the base sheet 20. Viewing in the planar direction, it can be seen that the positions of the absorbers 30 formed on one side 20A of the base sheet match the positions of the absorbers 30 formed on the other side 20B, and the positions of the fixing points 33 are also the same. The embodiment shown in FIG. 10(b) also has absorbers 30 formed on both sides of the base sheet 20. However, in contrast to the embodiment shown in FIG. 10(a), the positions of the absorbers 30 formed on one side 20A of the base sheet in the embodiment of FIG. 10(b) differ from the positions of the absorbers 30 formed on the other side 20B when viewed in the planar direction, and the positions of the fixing points 33 also differ. The embodiment shown in FIG. 10(a) exhibits a higher absorbency per absorber 30 compared to the above-described embodiment, and thus, liquid can be absorbed more "on the spot", i.e., with a smaller area of diffusion. Thus, the area causing leakage on the surface of the absorbent article can be reduced, which leads to the effect of improving surface dryness. The stretchability of the base sheet 20, however, is not impaired, because the ratio of the area of the fixing points 33 with respect to the area of the base sheet 20 is the same as that in the above-described embodiment. On the other hand, the embodiment shown in FIG. 10(b) allows the distance between adjacent absorbers 30 on each side of the base sheet 20 to be increased as compared to the above-described embodiment, assuming that the liquid absorbency is the same. This improves the liquid flowability through the spaces 40 on each side of the base sheet 20, which allows the liquid to be quickly drawn into the absorbers 30. Thus, the period of time in which fluid remains between the topsheet and the skin can be shortened, which leads to the effect of improving the ability to prevent fluid leakage. The stretchable absorbent cores 10 of the embodiments shown in FIGS. 10(a) and 10(b) can be produced by using the same pattern-indented roll as the first roll 401 also for the second roll 402 in the cutting device shown in FIG. 7(a).

In a stretchable absorbent core 10 according to the embodiment shown in FIG. 11, each absorber 30 constitutes a belt-like element extending in one direction within the planar direction of the base sheet 20, and the absorbers 30 are disposed according to a pattern in which those belt-like elements are formed in a multitude of rows and parallel to one another. The stretchable absorbent core 10 of this embodiment can be produced by cutting the fibers constituting the fibrous sheet 300 according to the pattern shown in FIG. 6(b). The stretchable absorbent core 10 of this embodiment exhibits stretchability mainly in a direction orthogonal to the direction in which the absorbers 30 are arranged. It is therefore preferable to incorporate the stretchable absorbent core 10 of this embodiment into an absorbent article in such a manner that the direction in which the absorbers 30 are arranged matches the width direction of the absorbent article. In some cases, however, it may be advantageous to incorporate the absorbent core into an absorbent article in such a manner that the direction in which the absorbers 30 are arranged matches the length direction of the absorbent article.

In the present invention, it is also possible to use an intermediate product in the process of producing the stretchable absorbent core 10 shown in FIG. 1—i.e., the intermediate product in the state shown in FIG. 8(a)—as still another embodiment of a stretchable absorbent core. In the stretchable absorbent core consisting of the intermediate product shown in FIG. 8(a), the absorber consists of an annular raised section located around a fixing point so as to surround that fixing point, as shown in the figure. In this stretchable absorbent core, the absorber consisting of the annular raised section is fixed to the base sheet only at the fixing point, and thus the shape of each absorber is not deformed upon stretch of the base sheet. Further, in this stretchable absorbent core, the fixing point has no absorber on it. Therefore, the volume of the spaces 40 in this embodiment is increased and thus liquid permeability is improved, assuming that the overhanging amount of the present absorber is the same as that of the overhang of each absorber in the stretchable absorbent core according to the embodiment shown in FIGS. 1 and 2. This is effective particularly for absorbing urine. Further, fluid that is excreted onto the fixing point is quickly absorbed "on the spot" by the annular raised section surrounding that fixing point, whereas fluid excreted between the absorbers is quickly diffused. In this way, it is possible to provide an absorption mechanism in which "on-the-spot" liquid absorption is combined with highly-diffusive liquid absorption. Further, it is possible to form a layer containing a large amount of air between the topsheet and the stretchable absorbent core, which leads to the effect of providing superior cushioning characteristics.

Although the present invention has been described according to preferred embodiments thereof, the invention is not to be limited to those embodiments. For example, instead of disposing the stretchable absorbent core 10 alone between the topsheet 101 and the backsheet 102 as in the foregoing embodiment, it is possible to also dispose a fiber stack made of pulp, or a fiber stack made of pulp and high-absorbent polymer, beneath the stretchable absorbent core 10.

INDUSTRIAL APPLICABILITY

The stretchable absorbent core of the present invention is superior in adaptability to a wearer's body and conformability to a wearer's movement, and a reduction in absorbency due to stretch is less likely to occur.

The invention claimed is:
1. A stretchable absorbent core comprising:
a base sheet having stretch property; and
a plurality of separate and independent absorbers disposed at least on one side of the base sheet,
wherein the absorbers are fixed to the base sheet through respective fixing points in such a design that the shape of each of the absorbers is not deformed upon stretch of the base sheet, wherein each of the absorbers is located on a respective one of the fixing points, wherein each of the absorbers is located on the fixing point in such a manner that a contour of the fixing point is encompassed within a contour of the absorber when viewed from above, wherein each of the absorbers is shaped so that it has an overhanging projection outwardly projecting from the fixing point in the planar direction, and wherein stretchability is exhibited between the fixing points.

2. The stretchable absorbent core according to claim 1, wherein the fixing points do not exhibit stretchability.

3. The stretchable absorbent core according to claim 1, wherein each of the absorbers is located around a respective one of the fixing points so as to surround that fixing point.

4. The stretchable absorbent core according to claim 3, wherein each of the absorbers contains annular raised sections formed in the thickness direction.

5. The stretchable absorbent core according to claim 1, wherein a space through which liquid can flow is provided between adjacent ones of the absorbers.

6. The stretchable absorbent core according to claim 1, wherein the absorbers are disposed on the base sheet across a planar direction thereof according to a regular, scattered pattern.

7. The stretchable absorbent core according to claim 1, wherein the absorbers are disposed according to a pattern in which belt-like elements extending in one direction are formed in a multitude of rows.

8. The stretchable absorbent core according claim 1, wherein an amount of 0.9-percent-by-weight sodium chloride solution the stretchable absorbent core can retain is equal to or above 0.1 g/g.

9. The stretchable absorbent core according to claim 1, wherein a total sum of an area of the fixing points as viewed from above is 5% to 95% with respect to an area of the base sheet.

10. An absorbent article comprising the stretchable absorbent core according to claim 1.

11. The stretchable absorbent core according to claim 1, wherein each of the absorbers is not fixed to the base sheet at the overhanding projection.

12. The stretchable absorbent core according to claim 1, wherein the overhanging projection is spaced from the base sheet.

* * * * *